(12) United States Patent
Groosman et al.

(10) Patent No.: US 8,962,909 B2
(45) Date of Patent: Feb. 24, 2015

(54) MOISTURE DETECTING MODULE AND A RECEIVING UNIT

(75) Inventors: Benno Groosman, Delft (NL); Tim Horeman, Delft (NL); Gerrit Vaandrager, Mijnsheerenland (NL)

(73) Assignee: Salusion IP B.V., Delft (NL)

( * ) Notice: Subject to any disclaimer, the term of this patent is extended or adjusted under 35 U.S.C. 154(b) by 377 days.

(21) Appl. No.: 13/382,830

(22) PCT Filed: Jul. 9, 2010

(86) PCT No.: PCT/NL2010/050444
§ 371 (c)(1),
(2), (4) Date: Mar. 6, 2012

(87) PCT Pub. No.: WO2011/005096
PCT Pub. Date: Jan. 13, 2011

(65) Prior Publication Data
US 2012/0165772 A1    Jun. 28, 2012

(30) Foreign Application Priority Data
Jul. 9, 2009    (NL) ..................................... 2003163

(51) Int. Cl.
*A61F 13/15*    (2006.01)
*A61F 13/42*    (2006.01)
(Continued)

(52) U.S. Cl.
CPC ........... *A61F 13/42* (2013.01); *A61F 2013/424* (2013.01); *A61F 2013/8479* (2013.01); *G01N 27/121* (2013.01)
USPC ...................................................... 604/361

(58) Field of Classification Search
CPC .............. A61F 13/42; A61F 13/47263; A61F 2013/421; A61F 2013/422; A61F 2013/423; A61F 2013/424; A61F 2013/426; A61F 2013/247; A61F 2013/428; A61F 2013/429; A61F 2013/8479
USPC ......................................................... 604/361
See application file for complete search history.

(56) References Cited

U.S. PATENT DOCUMENTS

| | | |
|---|---|---|
| 4,356,818 A | 11/1982 | Macias et al. |
| 4,738,260 A | 4/1988 | Brown |
| 4,800,370 A | 1/1989 | Vetecnik |

(Continued)

FOREIGN PATENT DOCUMENTS

| | | |
|---|---|---|
| BE | 902427 | 9/1985 |
| CA | 2562311 | 10/2004 |

(Continued)

OTHER PUBLICATIONS

PCT/NL2010/050444 International Search Report, mailing date Sep. 15, 2010.

*Primary Examiner* — Lynne Anderson
(74) *Attorney, Agent, or Firm* — Patterson Intellectual Property Law, P.C.; James R. Cartiglia

(57) ABSTRACT

The invention relates to a moisture detecting module for monitoring a moisture state of a napkin. The module comprises a moisture sensitive sensor and a moisture non-permeable layer covering the sensor. The moisture non-permeable layer is arranged for attachment to a napkin surface that, during use of the napkin by a person, is facing towards the person's skin such that the moisture sensitive sensor contacts the napkin surface. The moisture detection module is a RLC circuit that acts as a RF-tag thereby transmitting moisture information to a remote reading device.

20 Claims, 5 Drawing Sheets

(51) Int. Cl.
*A61F 13/84* (2006.01)
*G01N 27/12* (2006.01)

(56) References Cited

U.S. PATENT DOCUMENTS

| | | |
|---|---|---|
| 4,977,906 A | 12/1990 | Di Scipio |
| 5,043,704 A | 8/1991 | Blakeney |
| 5,092,860 A | 3/1992 | Pigneul |
| 5,354,289 A | 10/1994 | Mitchell et al. |
| 5,459,452 A | 10/1995 | DePonte |
| 5,542,941 A | 8/1996 | Morita |
| 5,579,765 A | 12/1996 | Cox et al. |
| 5,808,554 A | 9/1998 | Shuminov |
| 5,838,240 A | 11/1998 | Johnson |
| 5,903,222 A | 5/1999 | Kawarizadeh et al. |
| 5,908,411 A * | 6/1999 | Matsunari ............. 604/361 |
| 5,959,535 A | 9/1999 | Remsburg |
| 6,246,330 B1 | 6/2001 | Nielsen |
| 6,433,695 B1 | 8/2002 | Kai et al. |
| 6,559,772 B2 * | 5/2003 | Zand et al. ............. 340/604 |
| 6,580,013 B1 | 6/2003 | Belloso |
| 7,053,781 B1 | 5/2006 | Haire et al. |
| 7,145,053 B1 | 12/2006 | Emenike et al. |
| 2001/0053876 A1 * | 12/2001 | Torok et al. ............. 600/361 |
| 2002/0137307 A1 | 9/2002 | Kim et al. |
| 2002/0138061 A1 | 9/2002 | Nakaoka et al. |
| 2002/0145525 A1 | 10/2002 | Friedman et al. |
| 2003/0020615 A1 | 1/2003 | Zand et al. |
| 2003/0060789 A1 | 3/2003 | Shapira et al. |
| 2004/0030309 A1 | 2/2004 | Huang |
| 2004/0036484 A1 | 2/2004 | Tamai |
| 2004/0070510 A1 | 4/2004 | Zhang et al. |
| 2004/0207530 A1 | 10/2004 | Nielsen |
| 2004/0236302 A1 | 11/2004 | Wilhelm et al. |
| 2005/0178532 A1 | 8/2005 | Meng-Cheng et al. |
| 2005/0270162 A1 | 12/2005 | Hsieh |
| 2006/0061477 A1 | 3/2006 | Yeh |
| 2006/0266104 A1 | 11/2006 | Gordon |
| 2007/0013533 A1 | 1/2007 | Zazzara, Sr. et al. |
| 2007/0046482 A1 | 3/2007 | Chan et al. |
| 2007/0055210 A1 | 3/2007 | Kao |
| 2008/0058745 A1 | 3/2008 | Long et al. |
| 2008/0074274 A1 | 3/2008 | Hu et al. |
| 2008/0278336 A1 | 11/2008 | Ortega et al. |
| 2009/0302498 A1 * | 12/2009 | Nedestam ............. 264/263 |
| 2010/0136707 A1 * | 6/2010 | Kritzman et al. ......... 436/163 |

FOREIGN PATENT DOCUMENTS

| Country | Number | Date |
|---|---|---|
| CN | 101336857 | 1/2009 |
| DE | 4014213 | 11/1991 |
| DE | 4014572 | 11/1991 |
| DE | 4018953 | 1/1992 |
| DE | 4336728 | 5/1994 |
| DE | 202004008954 | 8/2004 |
| DE | 102004056379 | 4/2006 |
| DE | 102007015397 | 10/2008 |
| EP | 0270048 | 6/1988 |
| EP | 0606082 | 7/1994 |
| EP | 0813580 | 12/1997 |
| EP | 0911000 | 4/1999 |
| EP | 1063624 | 12/2000 |
| EP | 1242027 | 9/2002 |
| EP | 1263372 | 12/2002 |
| EP | 1393702 | 3/2004 |
| EP | 2002815 | 12/2008 |
| FR | 2765470 | 1/1999 |
| FR | 2788430 | 7/2000 |
| GB | 1154660 | 6/1969 |
| GB | 2102128 | 1/1983 |
| GB | 2250121 | 5/1992 |
| GB | 2272093 | 5/1994 |
| GB | 2306734 | 5/1997 |
| GB | 2321990 | 8/1998 |
| GB | 2325147 | 11/1998 |
| GB | 2348032 | 9/2000 |
| JP | 2297364 | 12/1990 |
| JP | 5180800 | 7/1993 |
| JP | 9290001 | 11/1997 |
| JP | 2001161732 | 6/2001 |
| JP | 2002153505 | 5/2002 |
| JP | 2004085277 | 3/2004 |
| JP | 2005323981 | 11/2005 |
| JP | 2006043389 | 2/2006 |
| JP | 2007007352 | 1/2007 |
| JP | 2007085817 | 4/2007 |
| JP | 2007132703 | 5/2007 |
| JP | 2008272331 | 11/2008 |
| KR | 20010053763 | 7/2001 |
| KR | 20020082593 | 10/2002 |
| NL | 1031745 | 11/2007 |
| NZ | 332717 | 2/2000 |
| PL | 20010349048 | 2/2001 |
| TW | 389691 | 5/2000 |
| WO | 9117730 | 11/1991 |
| WO | 9301781 | 2/1993 |
| WO | 9403817 | 2/1994 |
| WO | 9407224 | 3/1994 |
| WO | 9427539 | 12/1994 |
| WO | 9515795 | 5/1995 |
| WO | 9610265 | 4/1996 |
| WO | 9610976 | 4/1996 |
| WO | 9620681 | 7/1996 |
| WO | 9714127 | 4/1997 |
| WO | 9742613 | 11/1997 |
| WO | 9810390 | 3/1998 |
| WO | 9812997 | 4/1998 |
| WO | 9830179 | 7/1998 |
| WO | 9917692 | 4/1999 |
| WO | 9936021 | 7/1999 |
| WO | 9951179 | 10/1999 |
| WO | 9940420 | 12/1999 |
| WO | 9963497 | 12/1999 |
| WO | WO 00/16081 | 3/2000 |
| WO | 02078513 | 10/2002 |
| WO | 02101679 | 12/2002 |
| WO | 2004071363 | 8/2004 |
| WO | 2004100763 | 11/2004 |
| WO | 2005009311 | 2/2005 |
| WO | 2005020864 | 3/2005 |
| WO | 2005087163 | 9/2005 |
| WO | 2006058276 A2 | 6/2006 |
| WO | 2006134940 | 12/2006 |
| WO | 2007008122 | 1/2007 |
| WO | 2007027266 | 3/2007 |
| WO | 2007038990 | 4/2007 |
| WO | 2007067111 | 6/2007 |
| WO | 2007069964 | 6/2007 |
| WO | 2007098762 | 9/2007 |
| WO | 2007104081 | 9/2007 |
| WO | 2007125446 | 11/2007 |
| WO | 2008026092 | 3/2008 |
| WO | 2008026093 | 3/2008 |
| WO | 2008072118 | 6/2008 |

\* cited by examiner

MOISTURE DETECTING MODULE AND A RECEIVING UNIT

The invention relates to a moisture detecting module for monitoring a moisture state of a napkin, comprising a moisture sensitive sensor.

Such a moisture detecting module is e.g. known from the European patent publication EP 1 114 313 disclosing a system and an electronic sensor that interacts with an electromagnetic interrogation field so as to transmit local moisture information in a non-contacting way to a reading device.

The application of such a moisture detecting module enables a more efficient treatment of people that wear a napkin due to incontinence problems, e.g. elderly people, especially if said people can not actively indicate that a current napkin has to be replaced, either because they do not realize that the napkin is wet or are less able to warn a nurse.

When moisture is detected in the napkin, the reading device may generate a warning signal so that a nursing or caring professional is made aware that the napkin of the person has to be replaced.

However, in practice, the use of such a moisture detecting module might lead to inefficient use of napkins and superfluous replacement activities, since the detection of moisture does not always reflect the need of a napkin replacement properly. As an example, the absorbing capacity of the napkin is exploited in a minimal way.

It is an object of the invention to provide a moisture detecting module according to the preamble wherein the disadvantage mentioned above is counteracted. In particular, the invention aims at providing a moisture detecting module that indicates the need for a napkin replacement more reliably. Thereto, the moisture detecting module also comprises a moisture non-permeable layer covering the sensor, the moisture non-permeable layer being arranged for attachment to a napkin surface that, during use of the napkin by a person, is facing towards the person's skin such that the moisture sensitive sensor contacts the napkin surface.

By providing a moisture non-permeable layer that covers the sensor and is attached, during use, to the skin oriented surface of the napkin, the module is arranged such that moisture can reach the sensor merely via the napkin material below the module. Since moisture on the surface of the napkin that is in contact with the person's skin can not penetrate through the module, the sensor advantageously provides more reliable information as it senses the moisture when penetrating through napkin material below the surface that is covered by the moisture non-permeable layer. As a result, a moisture detection occurs only when the moisture absorbing capacity of the napkin is exploited at least partially, arriving at a moisture detecting module that indicates the need for a napkin replacement more reliably.

It is noted that patent publication WO 2006/058276 discloses a napkin provided with a moisture sensor partly covered by a moisture absorbent layer. Further, the napkin includes an electrical isolator arranged on a part of the sensor to avoid that electrical voltages or currents are applied to the user's skin.

It is further noted that patent publication US 2004/0236302 discloses an absorbent pant product including a humidity sensor. The sensor is arranged in a housing that is impermeable for moisture but permeable to gas particles.

Advantageous embodiments according to the invention are described in the following claims.

By way of example only, embodiments of the present invention will now be described with reference to the accompanying figures in which FIG. 1 shows a schematic cross sectional side view of a moisture detecting module according to the invention attached to a napkin;

It is noted that the figures show merely a preferred embodiment according to the invention. In the figures, the same reference numbers refer to equal or corresponding parts.

Figure 1:
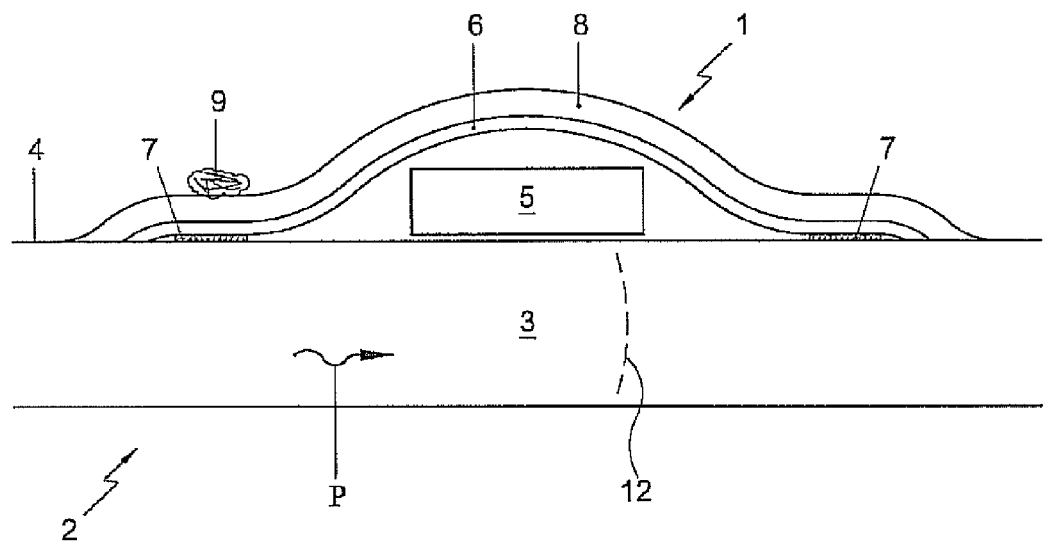

FIG. 1 shows a schematic cross sectional side view of a moisture detecting module 1 according to the invention. The module 1 is attached to a napkin 2 comprising a moisture absorbing section 3 and having a surface 4 that, during use of the napkin 2 by a person, is facing towards the person's skin. The moisture absorbing section 3 comprises e.g. a diaper or bed pad.

The module 1 comprises a moisture sensitive sensor 5 and a moisture non-permeable layer 6 covering the sensor 5. The moisture non-permeable layer 6 is provided with an adhesive layer 7 attached to the napkin surface 4, also called the inner napkin surface, such that the moisture sensitive sensor 5 contacts the napkin surface 4. It is noted that moisture non-permeable layer 6 can also be attached to the inner napkin surface 4 in another way, e.g. employing gripping elements.

Further, the moisture detecting module 1 comprises a comfort top layer 8 covering the moisture non-permeable layer 6 so that wearing the napkin 2 with the attached module 1 is more comfortable. Preferably, the comfort layer 8 comprises biocompatible material to counteract undesired physiological reactions on the skin, such as irritation reactions. Obviously, in principle, the module 1 can also be formed without a comfort top layer 8, thus providing a cheaper detection module, e.g. in case a bed pad is comprised by the moisture absorbing section 3.

On top of the moisture detecting module 1, moisture 9 might be present during use of the napkin 2. However, due to the presence of the moisture non-permeable layer 6, a premature detection of moisture 9, when the moisture absorbing capacity of the napkin 2 has not been exploited sufficiently, can be counteracted. Moisture may reach the sensor 5 only via the moisture absorbing section 3.

Figure 2:
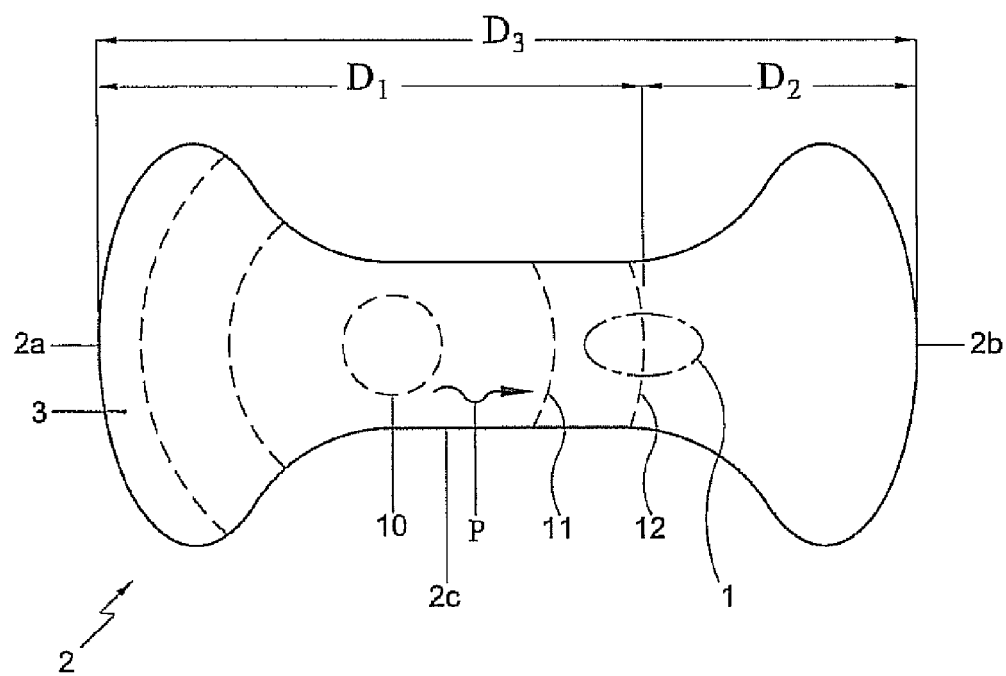
FIG. 2 shows a schematic top view of a napkin and the moisture detecting module of FIG. 1.

FIG. 2 shows a schematic top view of the moisture detecting module 1 and the napkin 2. The napkin 2 comprises a front section 2a for wearing adjacent the person's stomach and a back section 2b for wearing adjacent the person's back, and an intermediate section 2c connecting the front section 2a and the back section 2b. As shown, the moisture detecting module 1 is located in the intermediate section 2c, in an area that is closer to the back section 2*b* than to the front section 2*a*. By arranging the position of the moisture detecting module 1 such that a first distance D1 between the moisture detecting module 1 and the front section 2*a* is larger than a second distance D2 between the moisture detecting module 1 and the back section 2*b*, the moisture is advantageously detected when the moisture absorbing section 3 has absorbed a relatively large amount of moisture and the remaining absorbing capacity has become relatively small. As a result, no detection occurs when only a relatively small amount of moisture has been absorbed, thus efficiently employing the absorbing capacity of the napkin 2.

In another embodiment according to the invention, the module 1 is located such the first distance D1 is smaller than the second distance D2, so that a moisture detection occurs in an earlier stage, when the moisture has not yet penetrated a back part of the intermediate section 2*c*, so that the napkin 2 can be replaced earlier, thus improving the comfort of the person wearing the napkin 2.

Experiments have shown that a preferred location of the moisture detecting module 1 is in a range between circa ⅔ and circa ¾ relative to a third distance D3 between the front section and the back section. The inner bound of the range corresponds with a situation wherein the relative distance between the second distance D2 and the first distance D1 is circa ⅔, while the upper bound of the range corresponds with a situation wherein the relative distance between the second distance D2 and the first distance D1 is circa ¾. In said range, it appears that for most available napkins, the moisture detection occurs when the moisture absorbing section 3 has still some absorbing capacitance and the napkin 2 does not leak the moisture, thereby optimizing the use of napkins.

When the napkin 2 is worn by a person, the moisture absorbing section 3 absorbs moisture, such as urine. In a first stage, the moisture is localized in a first area 10 near the place where the moisture enters the moisture absorbing section 3. During time, the moisture penetrates further into the moisture absorbing section 3 since the absorbing capacity per area is limited. As shown in FIG. 2, the area that has absorbed the moisture grows gradually from the first area 10 along a penetration direction P to a second area 11 and then to a third area 12 reaching the location where the moisture detecting module 1 has been attached to the napkin. Once the moisture reaches the moisture sensitive sensor 3 that contacts the inner napkin surface 4, the moisture is detected. As such, a moisture state of the napkin 2 can be monitored. For use by people having specific incontinence or immobility issues, the sensor 5 could be placed elsewhere in the napkin. Optionally, one or a multiple number of additional sensors can be applied.

Figure 3:
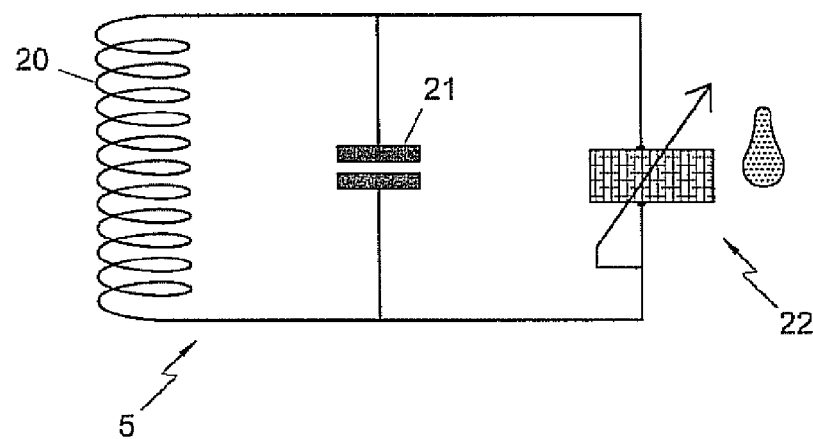
FIG. 3 shows a circuit of a sensor in a moisture detecting module according to a first embodiment according to the invention.

FIG. 3 shows a circuit of the moisture sensitive sensor 5 in a moisture detecting module 1 according to a first embodiment according to the invention. The circuit comprises a resonance circuit implemented as a coil 20 and a capacitor 21 that are interconnected in parallel. Further, a moisture sensitive resistor 22 is connected in parallel. If the resistive value of the resistor 22 is relatively high, the resonance circuit is tuned to a pre-defined resonance frequency, e.g. circa 8.2 MHz. However, if the resistive value of the resistor 22 is relatively low, the circuit looses its resonance characteristic since the coil 20 and the capacitor 21 are then short cut.

The moisture sensitive resistor 22 in FIG. 3 is arranged such that in dry condition the resistive value is high and in wet condition the resistive value is low. To that end, the resistor 22 includes material, such as cotton or cellulose that becomes electrically conducting in wet condition. Obviously, any material can be used that has electrically conducting characteristics when being wet, e.g. salt or a specific polymer. As a consequence, the resonance characteristic vanishes if the resistor 20 is contacted by moisture emerging from the moisture absorbing section 3. As such, the moisture sensitive sensor is arranged for being deactivated if a predefined moisture degree is exceeded.

Figure 4:
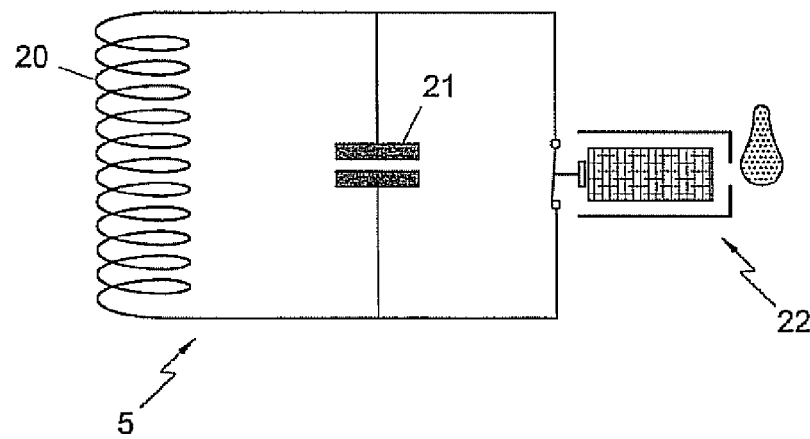
FIG. 4 shows a circuit of a sensor in a moisture detecting module according to a second embodiment according to the invention.

FIG. 4 shows a circuit of the moisture sensitive sensor 5 in a moisture detecting module 1 according to a second embodiment of the invention. The circuit is arranged similar to the circuit as shown in FIG. 3. However, in FIG. 4, the moisture sensitive resistor 22 is arranged such that in dry condition the resistive value is low and in wet condition the resistive value is high. To that end, the resistor 22 includes material that expands in wet condition, thereby electrically disconnecting the ends of the resistor 22. As an example, said material may include pressurized cotton. As a consequence, the resonance characteristic becomes active when the resistor 20 is contacted by moisture emerging from the moisture absorbing section 3. As such, the moisture sensitive sensor is arranged for being deactivated if a predefined moisture degree is exceeded.

Figure 5:
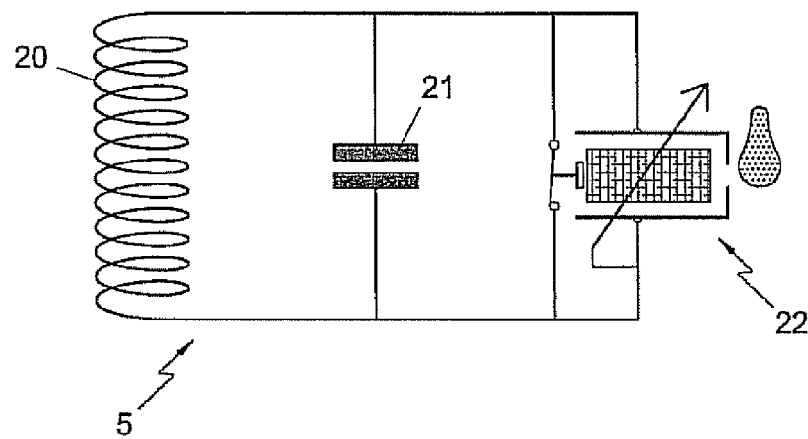
FIG. 5 shows a circuit of a sensor in a moisture detecting module according to a third embodiment according to the invention.

FIG. 5 shows a circuit of the moisture sensitive sensor 5 in a moisture detecting module 1 according to a third embodiment of the invention. The circuit is arranged similar to the circuit as shown in FIG. 4. Also the moisture sensitive resistor 22 is arranged such that in dry condition, in a first state, the resistive value is low, so that the resonance characteristic vanishes, and that in wet condition, in a second state, the resistive value becomes high, so that the resonance characteristic is active. In addition, when the resistor 22 remains wet during a certain time period, in a third state, the resistive value becomes low again, thereby short cutting the resonance circuit. As such, the moisture sensitive sensor is arranged for being deactivated when a predefined time period has lapsed after the sensor has been activated.

Figure 6A:
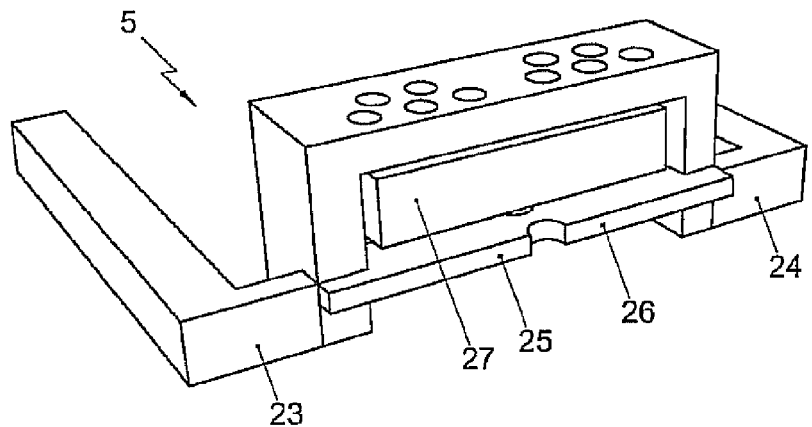
FIG. 6a shows a schematic perspective view of the sensor of FIG. 5 in a first state.
Figure 6B:
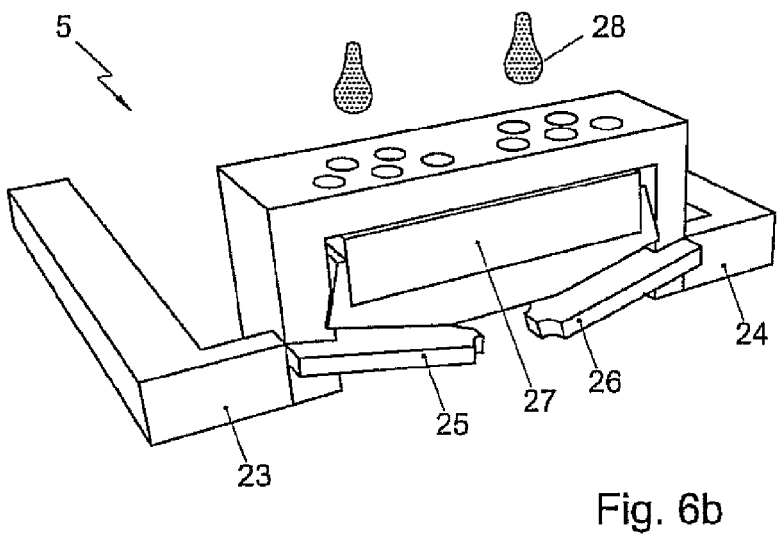
FIG. 6b shows a schematic perspective view of the sensor of FIG. 5 in a second state.
Figure 6C:
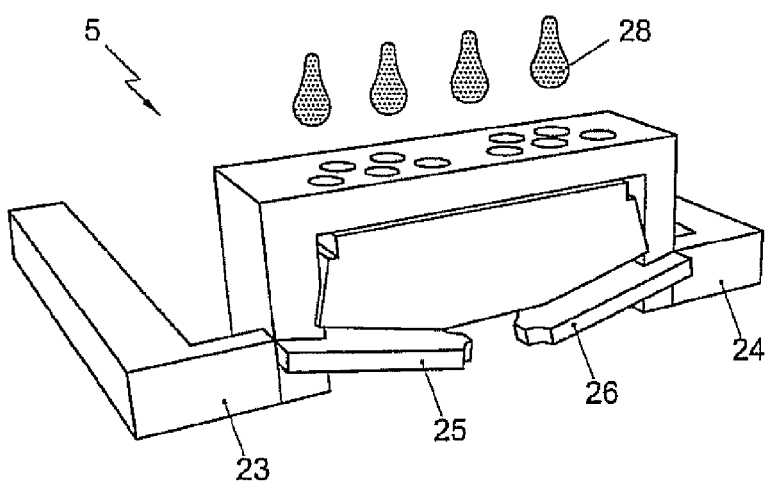
FIG. 6c shows a schematic perspective view of the sensor of FIG. 5 in a third state.

FIGS. 6*a-c* show a schematic perspective view of the sensor 5 of FIG. 5 its first, second and third state, respectively. The sensor comprises two ends 23, 24 that are in an electrically conduction state when the sensor is in the first, dry condition, see FIG. 6*a*, by means of the physically abutting tips 25, 26 that are connected to the first and second ends 23, 24, respectively. Further, the sensor 5 comprises a cotton layer 27 that is contained in a cavity and abuts against the tips 25, 26. In the second state, see FIG. 6*b*, the cotton layer 27 expands due to the absorbance of moisture 28 into the direction of the tips 25, 26, thereby deforming the tips 25, 26, such that their mutual physical contact is broken and the ends 23, 24 are electrically disconnected. In this second state, the sensor is thus activated. Further, in the third state, see FIG. 6*c*, the cotton layer 27 is saturated by the moisture 28 and electrically connects the tips 25, 26 again, so that the sensor is deactivated. As a result, also a warning signal, such as an acoustic signal, generated by an external reading device may stop.

During use of the moisture detecting module 1 according to the invention, the passive resonance circuit interacts with an electromagnetic interrogation field so as to transmit local moisture information in a non-contacting way to a reading device 31.

Figure 7:
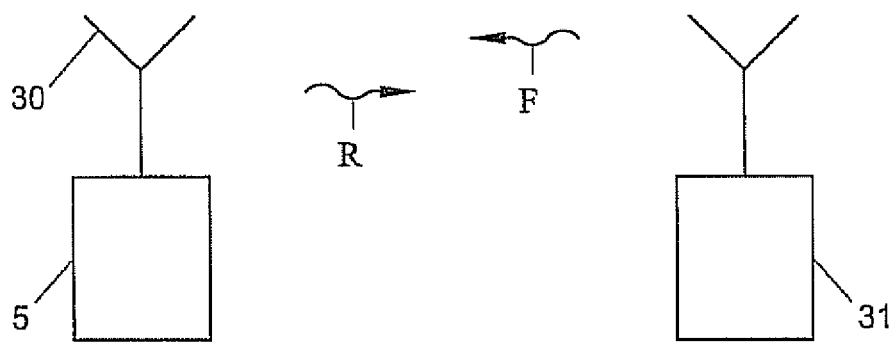
FIG. 7 shows a schematic view of a reading device according to the invention.

FIG. 7 shows a schematic view of a reading device 31 according to the invention. The reading device 31 generates an interrogating electromagnetic field F, e.g. a signal having fixed RF frequency of e.g. circa 8.2 MHz, or a signal having a sweeping frequency ranging from circa 7.7 MHz and circa 8.7 MHz. When the sensor 5 is activated, having a resonance characteristic, the circuit acts as a RF transmission element, also called RF tag, transmitting an electromagnetic response signal R that is received by the reading device 31, thereby obtaining a wireless RF moisture detecting system for monitoring a moisture state of a napkin.

Figure 8:
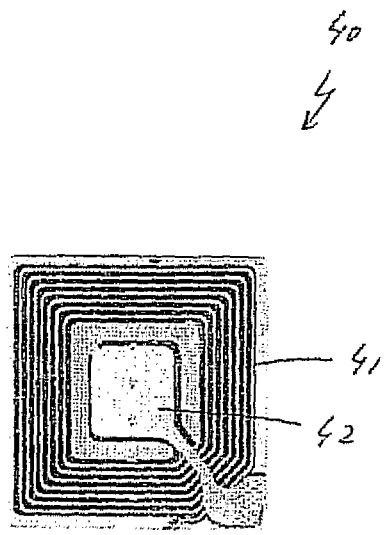
FIG. 8 shows a schematic view of a further embodiment of a sensor in a moisture detecting module in a further embodiment according to the invention.

FIG. 8 shows a schematic view of a further embodiment of a sensor in a moisture detecting module in a further embodiment according to the invention. The sensor comprises a passive RF tag 40 including a coil 41 and a capacitor 42 arranged in parallel, tuned to a specific RF resonance frequency, e.g. circa 8.2 MHz. However, as will be apparent to the person skilled in the art, in another embodiment the sensor can be set to another RF resonance frequency. The shown sensor is of the so-called EAS tag type. In a dry state, the tag provides an electromagnetic response signal R. When the tag becomes wet, short circuits electrically connect parts of the coil, thereby causing that the response signal of the tag becomes weaker and weaker and eventually may even be so weak that it cannot be detected anymore. By using a passive RF tag that is sensitive to moisture, a cheap but effective implementation of the sensor is obtained.

The invention is not restricted to the embodiments described herein. It will be understood that many variants are possible.

Instead of applying a passive resonance circuit, the moisture detecting module can also be provided with an active resonance circuit. Further, the module can be arranged with another transmission element type, such as an active strip antenna.

Further, if it is desired to switch off the resonance circuit externally, a local electromagnetic field may be applied having a relatively high field strength, thereby irreversibly damaging the circuit structure of the coil 20.

It is noted that the sensor, instead of using a moisture sensitive resistor may be arranged for detecting moisture in another way, e.g. by sensing a moisture dependent capacitor, sensing an electrolytic device converting water into hydrogen and oxygen, the required electrical current being a measure of the water amount, sensing moisture dependent resonance material (piezo-electrical effect), sensing heat conducting variations, sensing material deformation, and/or sensing optical variations including sensing a chilled mirror, i.e. measuring droplets on a mirror having a varying temperature.

In addition, a supplementary layer can be applied between the sensor 5 and the surface 4, that, during use of a napkin 2, is facing towards the person's skin, thus forming a buffer and/or visual cover of the sensor 5. The supplementary layer can e.g. be implemented as a moisture permeable covering layer.

It is further noted that the moisture detecting module can not only be used in combination with a napkin, but also with other product wherein a moisture state has to be monitored, e.g. a banding, dressing or a liquid conducting device, such as pipe having a seam.

Other such variants will be obvious for the person skilled in the art and are considered to lie within the scope of the invention as formulated in the following claims.

The invention claimed is:

1. A moisture detecting module for monitoring a moisture state of a napkin, comprising a moisture sensitive sensor and a moisture non-permeable layer covering the sensor, the moisture non-permeable layer being arranged for attachment to a napkin surface that, during use of the napkin by a person, is facing towards the person's skin such that the moisture sensitive sensor contacts the napkin surface.

2. A moisture detecting module according to claim 1, further comprising a comfort top layer covering the moisture non-permeable layer.

3. A moisture detecting module according to claim 2, wherein the moisture non-permeable layer is provided with an adhesive layer for attachment to the napkin surface.

4. A moisture detecting module according to claim 2, wherein the moisture sensitive sensor is arranged for being deactivated if a predefined moisture degree is exceeded.

5. A moisture detecting module according to claim 2, wherein the moisture sensitive sensor is arranged for being activated if a predefined moisture degree is exceeded.

6. A moisture detecting module according to claim 2, wherein the comfort top layer comprises biocompatible material.

7. A moisture detecting module according to claim 6, wherein the moisture non-permeable layer is provided with an adhesive layer for attachment to the napkin surface.

8. A moisture detecting module according to claim 6, wherein the moisture sensitive sensor is arranged for being deactivated if a predefined moisture degree is exceeded.

9. A moisture detecting module according to claim 6, wherein the moisture sensitive sensor is arranged for being activated if a predefined moisture degree is exceeded.

10. A moisture detecting module according to claim 1, wherein the moisture non-permeable layer is provided with an adhesive layer for attachment to the napkin surface.

11. A moisture detecting module according to claim 10, wherein the moisture sensitive sensor is arranged for being deactivated if a predefined moisture degree is exceeded.

12. A moisture detecting module according to claim 1, wherein the moisture sensitive sensor is arranged for being deactivated if a predefined moisture degree is exceeded.

13. A moisture detecting module according to claim 1, wherein the moisture sensitive sensor is arranged for being activated if a predefined moisture degree is exceeded.

14. A moisture detecting module according to claim 13, wherein the moisture sensitive sensor is arranged for being deactivated when a predefined time period has lapsed after the sensor has been activated.

15. A moisture detecting module according to claim 1, further comprising a transmission element for transmitting an electromagnetic signal.

16. A moisture detecting module according to claim 15, wherein the transmission element comprises a passive resonance circuit.

17. A napkin, comprising a moisture absorbing section and a surface that is oriented away from the moisture absorbing section and, during use of the napkin by a person, is facing towards the person's skin, the napkin further comprising a moisture detecting module according to claim 1, wherein the moisture sensitive sensor contacts the napkin surface.

18. A napkin according to claim 17, comprising a front section for wearing adjacent the person's stomach and a back section for wearing adjacent the person's back, wherein the distance between the moisture detecting module and the front section is larger than the distance between the moisture detecting module and the back section.

19. A napkin according to claim 18, wherein the moisture detecting module is located in a range being from ⅔rds to ¾ths the distance between the front and back sections.

20. A reading device for reading an electromagnetic signal transmitted by a transmission element comprised by a moisture detecting module for monitoring a moisture state of a napkin, the module comprising a moisture sensitive sensor and a moisture non-permeable layer covering the sensor, the moisture non-permeable layer being arranged for attachment to a napkin surface that, during use of the napkin by a person, is facing towards the person's skin such that the moisture sensitive sensor contacts the napkin surface.

* * * * *